United States Patent
Yu et al.

(10) Patent No.: US 11,328,825 B1
(45) Date of Patent: May 10, 2022

(54) MACHINE LEARNING TECHNIQUES FOR IDENTIFYING OPPORTUNITY PATIENTS

(71) Applicant: IQVIA Inc., Parsippany, NJ (US)

(72) Inventors: Kezi Yu, King of Prussia, PA (US); Fan Zhang, Plymouth Meeting, PA (US); Yunlong Wang, Malvern, PA (US); Yilian Yuan, North Wales, PA (US); Emily Zhao, Wayne, PA (US); William McClellan, Collegeville, PA (US); Yong Cai, Bala Cynwyd, PA (US)

(73) Assignee: IQVIA Inc., Parsippany, NJ (US)

( * ) Notice: Subject to any disclaimer, the term of this patent is extended or adjusted under 35 U.S.C. 154(b) by 248 days.

(21) Appl. No.: 16/847,562

(22) Filed: Apr. 13, 2020

(51) Int. Cl.
| | | |
|---|---|---|
| G16H 50/70 | (2018.01) |
| G16H 10/60 | (2018.01) |
| G16H 40/20 | (2018.01) |
| G16H 50/20 | (2018.01) |
| G16H 20/10 | (2018.01) |
| A61B 5/00 | (2006.01) |

(52) U.S. Cl.
CPC .......... *G16H 50/70* (2018.01); *A61B 5/4848* (2013.01); *A61B 5/7267* (2013.01); *G16H 10/60* (2018.01); *G16H 20/10* (2018.01); *G16H 40/20* (2018.01); *G16H 50/20* (2018.01)

(58) Field of Classification Search
CPC ................................................ G06Q 50/20–26
See application file for complete search history.

(56) References Cited

U.S. PATENT DOCUMENTS

| | | | |
|---|---|---|---|
| 2009/0234626 A1* | 9/2009 | Yu ........................... G16H 50/50 703/11 |
| 2009/0234628 A1* | 9/2009 | Yu ......................... A61N 5/1031 703/11 |
| 2017/0196497 A1* | 7/2017 | Ray .......................... A61B 5/11 |
| 2019/0246990 A1* | 8/2019 | Karoly ................. A61B 5/0205 |

* cited by examiner

*Primary Examiner* — Neal Sereboff
(74) *Attorney, Agent, or Firm* — Fish & Richardson P.C.

(57) ABSTRACT

Systems and techniques are disclosed for using machine-learning to identify potential opportunity patients that are more likely to adjust his/her preference for a healthcare provider or service. In some implementations, integrated patient data is obtained. A patient sequence feature vector, a provider sequence feature vector, and a set of entity-specific feature vectors are generated. A set of opportunity patients is identified. A notification is transmitted to the set of opportunity patients about a second treatment plan.

14 Claims, 7 Drawing Sheets

MACHINE LEARNING TECHNIQUES FOR IDENTIFYING OPPORTUNITY PATIENTS

FIELD

The present specification relates to technology for performing data analysis, and more specifically, predictive analytics.

BACKGROUND

Data aggregation can include compiling data from multiple different sources. Depending on the characteristics of the sources from which the data is being compiled, there can be challenges with processing the data to identify data patterns. For example, data obtained from disparate data sources can be in different incompatible formats that require significant processing capabilities to analyze together. Further, there may be restrictions or other factors that limit access to data from certain providers. Once the data is obtained, from multiple different disparate sources, it can be difficult to effectively present that data in a user interface, particularly, when the data obtained will differ on a per-user basis.

SUMMARY

In general, innovative aspects of the subject matter described in this specification can be embodied in systems and techniques that utilize machine-learning techniques to identify potential opportunity patients that are more likely to adjust his/her preference for a healthcare provider or service. For example, a system can apply a deep learning framework to predictively identify patients, from among a population of patients associated with a healthcare network, that are more likely to change their primary care physicians.

The system can generate predictions before patients change their physicians so that data or information that may be useful in guiding the adjustment process can be provided to the patients at specified time points. In this way, the predictive capabilities of the system can be used to output data to specific patients in specific circumstances in a manner that increases awareness of a particular medication or treatment option, provides patients with details on subsequent actions to be taken, and improves upon patient targeting techniques for various purposes.

The systems and techniques described herein can provide various types of technical advantages over the use of other techniques to generate predictions relating to healthcare data. For example, techniques that use machine learning models to predict patients to target may require extensive manual feature engineering. Specifically, these techniques may focus on a single type of data and may not leverage insights that may be derived from evaluating different types of healthcare data in parallel to identify opportunities within a patient population. As a result, these techniques may fail to identify data attributes and/or features that become identifiable under a generalized context provided by systematic evaluation of different data types. For example, considering a patient's treatment plan alone may prevent the identification of patterns that are related to prescribing activity of the physician that treats the patient. In contrast, by evaluating patient treatment patterns in combination with prescriber patterns, the techniques disclosed herein enable cross-correlation of different data types corresponding to related events and/or circumstances (e.g., a patient visit in which patient data and prescriber data are both captured).

In one general aspect, subject matter described in this specification may be embodied in a method that includes the following operations. For example, the operations can include obtaining integrated patient data for multiple patients. In this example, the integrated patient data includes different types of information associated with a treatment plan. The method can also include generating a plurality of feature vectors including a feature vector corresponding to each of the different types of information associated with the treatment plan. Additionally, the method includes identifying a set of opportunity patients from among the multiple patients based on applying a combining model to the plurality of feature vectors. The combining model is trained to classify patients as being likely to adjust the treatment plan. The method also includes providing data indicating the set of opportunity patients for output.

One or more implementations can include the following optional features. For instance, in some implementations, the different types of information include patient sequence information identifying treatment events associated with a treatment plan, provider sequence information identifying providers that have participated in a treatment event associated with the treatment plan, and a set of entity-specific attributes associated with the treatment plan.

In some implementations, generating the plurality of feature vectors corresponding to each of the different types of information associated with the treatment plan additional operations. For example, the generation includes generating a patient sequence feature vector corresponding to the patient sequence information based on applying a first model to the patient sequence information. In this example, the first model is trained to output patient sequence feature vectors for respective patients with different patient sequences. Additionally, the generation includes generating a provider sequence feature vector corresponding to the provider sequence information based on applying a second model to the provider sequence information. The second model is also trained to output provider sequence feature vectors for respective providers with different provider sequences.

In some implementations, the multiple patients are each enrolled in the treatment plan. In such implementations, the treatment plan represents treatment of a disease condition using a pharmaceutical product. Additionally, the patient sequence information identifies, for each patient included in the multiple patients, a first treatment event indicating diagnosis of the disease condition, a second treatment event indicating a prescription of the pharmaceutical product, and a third treatment event indicating a treatment follow-up. The set of opportunity patients also represents patients, from among the multiple patients that are classified by the combining model as being likely to withdraw from the treatment plan based on data associated with the first treatment event, the second treatment event, or the third treatment event.

In some implementations, generating the plurality of feature vectors corresponding to each of the different types of information associated with the treatment plan includes generating a set of entity-specific feature vectors corresponding to the set of entity-specific attributes based on applying a third model to the set of entity-specific attributes. In such implementations, the third model is trained to output sets of entity-specific feature vectors for respective sets of entity-specific attributes.

In some implementations, the first model and the second model each include recurrent neural networks. In such implementations, the third model and the combining model each include deep neural networks.

In some implementations, the method includes a set of additional operations. For instance, the method includes identifying a set of opportunity providers associated with the integrated patient data based on applying the combining model to data indicating the patient sequence feature vector, the provider sequence feature vector, and the set of entity-specific feature vectors. In such implementations, the combining model is trained to classify providers as being likely to adjust the treatment plan.

In some implementations, the set of entity-specific attributes includes provider-level attributes, patient-level attributes, and plan-level attributes. In such implementations, the set of entity-specific feature vectors includes a provider-level feature vector, a patient-level feature vector, and a plan-level feature vector.

In some implementations, the set of opportunity patients includes one or more patients classified by the combining model as being likely to adjust a pharmaceutical product associated with the treatment plan.

In some implementations, the set of opportunity patients includes one or more patients classified by the combining model as being likely to adjust a provider associated with the treatment plan.

Other versions include corresponding systems, apparatus, and computer programs, configured to perform the actions of the methods encoded on computer storage devices.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

In the drawings, like reference numbers represent corresponding parts throughout.

DETAILED DESCRIPTION

Figure 1A:
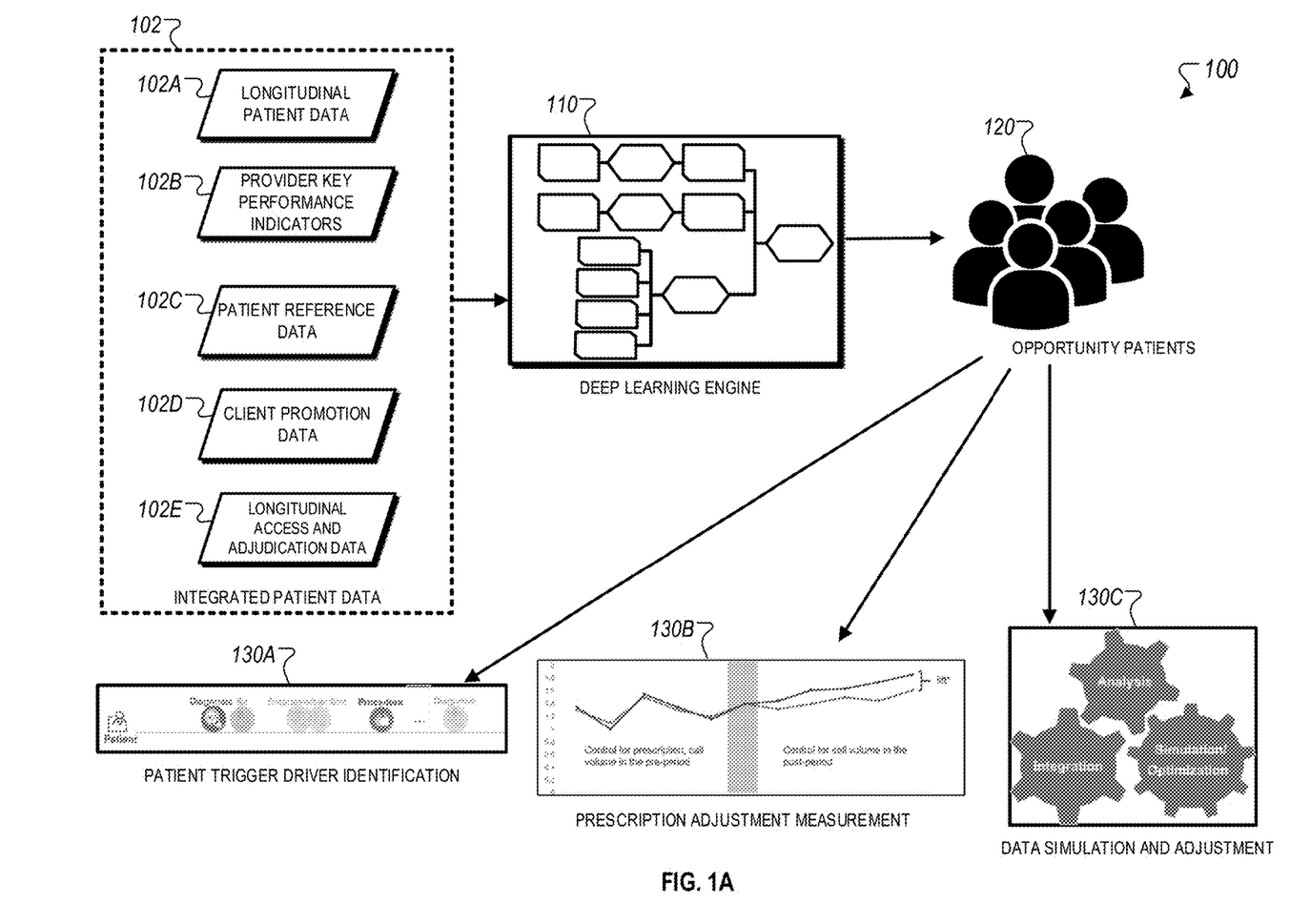
FIG. 1A illustrates an example of a system that can identify opportunity patients and/or opportunity events based on applying a deep learning engine to recognize patterns within integrated patient data.

FIG. 1A illustrates an example of a system 100 that can identify opportunity patients and/or opportunity events based on applying a deep learning engine to recognize patterns within integrated patient data. The system 100 includes a deep learning engine 110 that is configured to process and evaluate integrated patient data 102 obtained from multiple data sources (e.g., a hospital, a private medical practice, a hospital, a pharmaceutical manufacturing company). The integrated patient data 102 includes longitudinal patient data 102A, provider key performance indicators 102B, patient reference data 102C, client promotion data 102D, and longitudinal access and adjudication data 102E.

Longitudinal patient data 102A includes information from an electronic medical record, such as a patient's treatment plan for a diagnosed condition, a sequence of patient visits, medications prescribed to the patient, health metrics collected during patient visits, among others. Provider key performance indicators 102B include metrics used to monitor, analyze, or improve relevant healthcare processes to increase patient satisfaction (e.g., average hospital stay, treatment costs, hospital readmission rates, patient wait time, patient safety, payer costs). Patient reference data 102C can include a set of healthcare standards used to evaluate treatment provided to a patient (e.g., to determine whether treatment provided to a patient meets the standard of care for the corresponding treatment). Client promotion data 102D can include information related to medication pricing, industry service offerings, customer satisfaction surveys, among other types of data related to the competitive landscape of healthcare services. Longitudinal access and adjudication data 102E can include payer information associated with healthcare services. These different types of data included within the integrate patient data 102 enable the deep learning engine 110 to evaluate a different aspect of healthcare services provided to patients to enable a comprehensive analysis in determining opportunity patients, as discussed throughout.

Figure 1B:
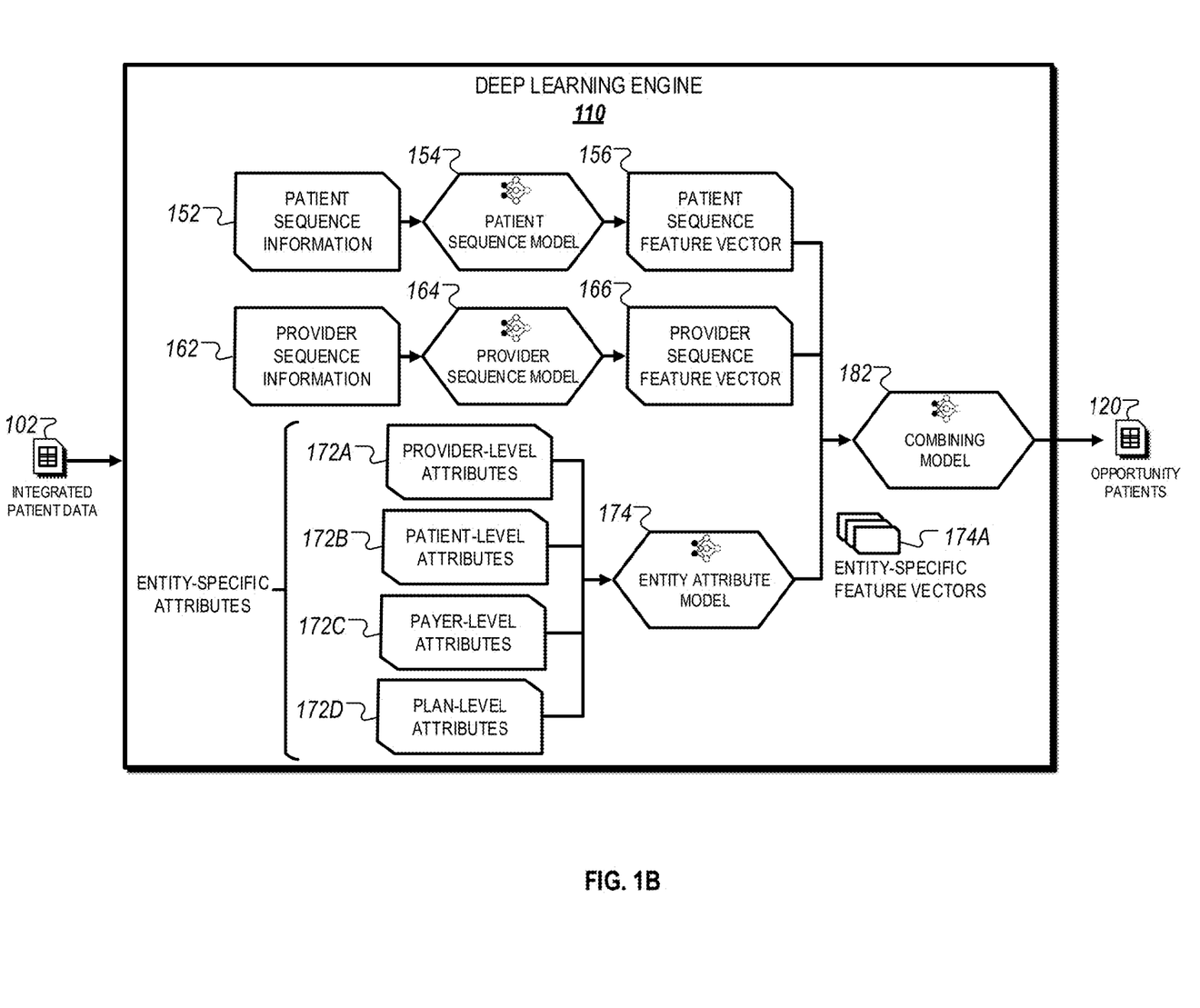
FIG. 1B illustrates an example of an architecture for the deep learning engine illustrated in FIG. 1A.

The deep learning engine 110 is trained to apply various machine learning techniques to process each of the types of information specified in the integrated patient data 102, as described in reference to FIG. 1B. The architecture of the deep learning engine 110 enabling this processing is described in reference to FIG. 1B. Specifically, the deep learning engine 110 recognizes and evaluates data patterns within the integrated patient data 102 to identify a set of opportunity patients. As described herein, an "opportunity patient" refers to an individual that is predicted by the deep learning engine 110 to make a change to an existing healthcare service. As an example, an opportunity patient can be an individual identified by the deep learning engine to be likely to change his/her primary care physician. As another example, an opportunity patient can be an individual that is identified to be likely to change a medication for a treatment condition. In other examples, the change can be related to other aspects of healthcare services, such as changes to a health insurance plan, changes to affiliations with a provider network, among others.

In some instances, the system 100 can also identify opportunity events. As described herein, an "opportunity event" refers to an event within a patient's treatment sequence that is identified by the deep learning engine 110 to likely cause a change to the patient's existing healthcare service. For example, an opportunity event can be a patient survey indicating that he/she is dissatisfied with service received by his/her primary care physician. As another example, an opportunity event can be a hospitalization event that occurs due to a patient experiencing side effects after taking a medication. Opportunity events can be used to identify corresponding opportunity patients. For example, a patient can be identified to be an opportunity patient if his/her treatment plan includes a subsequent event that is identified to be an opportunity event.

Additionally, though FIG. 1A shows the identification of opportunity patients, in some implementations, the deep learning engine 110 can additionally (or alternatively) be capable of identifying other types of opportunity individuals. For instance, as discussed in reference to FIG. 4, the deep learning engine 110 can identify opportunity providers, which refer to providers that are predicted to make a change to a healthcare service provided to patients. As an example, a provider that is likely to prescribe a new medication brand to patients can be identified as an opportunity provider for the new medication brand.

The identification of opportunity providers enables targeting techniques to be applied to these providers to increase the number of prescriptions of the target medication (and thereby increase brand awareness). Opportunity providers can be identified in a similar manner as discussed throughout for identifying opportunity patients. For example, the deep learning engine 110 can process provider sequence data to identify the occurrence of certain treatment events indicating that a provider is likely to create a change to his/her practice (e.g., issue a new type of medication, perform a new medical procedure).

The system 100 enables different predictive capabilities based the identification of opportunity patients. In the first example shown in FIG. 1A, the system 100 identifies patient triggers 130A. In this example, the system 100 evaluates patient treatment sequences of opportunity patients to identify events that are more likely to trigger an opportunity event (i.e., events that are more reflect that the patient is more likely to make an adjustment relating to his/her healthcare services). For instance, in this example, the deep learning engine 110 can use natural language processing and semantic analysis to identify events demonstrating that the patient is unsatisfied, unhappy, or looking for a different experience (making him/her more likely to make a change to his/her medical services).

In the second example shown in FIG. 1A, the system 100 prospectively measures anticipated prescription adjustment parameters 130B. For instance, as shown in the figure, the system 100 monitors a number of calls placed by patients or providers to make prescription orders before an opportunity event during which a patient is predicted to make an adjustment to his/her existing medication plan (e.g., dosage reduction). The system 100 then predicts a lower call volume associated with predictions after the opportunity event. This adjustment can then be used to adjust resource allocation amongst all patients associated with a healthcare network. For example, resources that would have been dedicated to responding to calls from opportunity patients to order prescriptions issued by providers can be diverted to other patients that are not identified as opportunity patients. In this way, predictions related to opportunity patients enables the preemptive execution of actions that can then be used to realize efficiencies resulting from changing patient behaviors.

In the third example shown in FIG. 1A, the system 100 enables data simulation and adjustment 130C based on identifying the opportunity patients 120. For instance, as discussed above, identifying opportunity patients and/or opportunity events enables the system 100 to identify anticipated changes in patient-level behavior. Such patient-level behavior can be aggregated to identify changes to system-level affects. For example, if many patients are predicted to opt out of a health savings program, then this prediction can be used to adjust future resource allocation for all health services programs so that resources allocated to managing the health savings program is reduced.

The system 100 can also run data simulations 130C on the adjusted resource allocation to determine whether any adverse impacts would result for patients that do not opt out of the health savings programs due to the reduced budget allocation. As another example, if a large number of patients are expected to be prescribed a new medication that is not distributed through a healthcare network, then the system 100 can generate a model to represent new prescribing activity associated with the new medication, and use the model to determine whether the healthcare network has the capacity to support new shipments of the new medication from the manufacturer. In this example, data simulations 130C using the generated model can be used to perform improve capacity building when extending healthcare services to a new medication that is not presently supported.

FIG. 1B illustrates an example of an architecture for the deep learning engine 110 illustrated in FIG. 1A. The deep learning engine 110 includes various machine learning models, such as a patient sequence model 154, a provider sequence model 164, an entity attribute model 174, and a combining model 182.

The machine learning models generally can be used to generate feature vectors with respect to a specific type of data within the integrated patient data 102 (which is obtained and aggregated from multiple data sources). As described herein, a "feature" represents an individual measurable property or characteristic of a phenomenon being observed. For example, a feature can represent a medication that is prescribed to a patient for a treatment of a medical condition. A "feature vector" represents a set of numeric features. For example, the patient feature vector 156 can be used to reach a two-way classification as to whether patient sequence information 152 includes a pattern associated with opportunity patients (e.g., a number of prescribed medications exceeding a threshold and thereby indicating that a corresponding treatment plan is ineffective). As another example, the provider sequence feature vector 166 can be used to reach a two-way classification as to whether provider sequence information 162 includes a pattern associated with opportunity patients (e.g., a number of negative sentiment reviews left for a provider exceeding a threshold and thereby indicating that the patient is likely dissatisfied with service provided by the provider).

The patient sequence model 154 is used to evaluate patient sequence information 152 to generate a patient sequence feature vector 156. The patient sequence information 152 includes information associated with a treatment plan of the patient (e.g., medical history data, medication data, patient visit data). The patient sequence feature vector 156 identifies features recognized by the patient sequence model 154 in the patient sequence information 152 indicating a trigger or driver of an opportunity patient (e.g., a patient changing a provider, prescription, being diagnosed with a different condition).

The provider sequence model 164 is used to evaluate provider sequence information 162 to generate a provider sequence feature vector 166. The provider sequence information 162 includes information associated with a provider's treatment activity (e.g., prescriptions issued, patients treated, diagnoses issued, procedures performed). The provider sequence feature vector 166 identifies features recognized by the provider sequence model 164 in the provider sequence information 162 indicating a trigger or driver of an opportunity provider (e.g., a provider that is likely to prescribe a new medication, a provider expanding his medical practice, patient referral to a specialist).

The entity attribute model 174 is used to evaluate attribute data (e.g., provider-level attributes 172A, patient-level attributes 172B, payer-level attributes 172C, plan-level attributes 172D) for different participants and/or plans associated with a healthcare network. The entity attribute model 174 generates entity-specific feature vectors 174A based on this evaluation. Each of the entity-specific feature vectors 174A includes classifier information that is used to evaluate, for example, routine data patterns for a given entity (or entity type), or data patterns for representing anomalous data patterns for the given entity. The feature vectors 174A are "entity-specific" in that they are customized for an entity for which predictions are to be generated using the deep learning engine 110. For example, if the entity to receive the opportunity patient predictions is a medication manufacturer, then the opportunity patients are identified with respect to the likelihood of a patient to change a medication, which is then reflected in the provider-level attributes 172A, patient-level attributes 172B, the payer-level attributes 172C, and the plan-level attributes 172D used by the entity attribute model 174 to generate the entity-specific feature vectors 174A. As another example, if the entity to receive the opportunity patient predictions is a healthcare management organization that manages providers within a provider network, then the opportunity patients are identified with respect to the likelihood of a patient to change a healthcare provider. In this way, the entity attribute model 174 generates feature vectors that are specific to the desired predictions requested by a specific entity.

The combining model 182 can be used to combine features identified in the patient sequence feature vector 156, the provider sequence feature vector 166, and the entity-specific feature vectors 174A, and identify opportunity patients 120. Specifically, the combining model 182 combines features for an individual patient to compute an overall likelihood that the individual patient is classified as an opportunity patient. As discussed throughout, opportunity patients 120 can be identified based on predicting a likelihood that patients will make a change to a healthcare service. The likelihood can be represented as a probabilistic value (e.g., between 0.0 and 1.0) in the form of a score computed based on the features specified in the patient sequence feature vector 156, the provider sequence feature vector 166, and the entity-specific feature vectors 174A. For example, the score for a patient can be 0.96 (i.e., 96% likelihood that the patient will subsequently change a healthcare service) based on a particular feature included in the patient sequence feature vector 156. In this example, the feature can indicate that the patient has repeatedly requested to change his/her current medication, which is then used to predict a high likelihood of prescription adjustment in the future.

The patient sequence model 154 and the provider sequence model 164 can be trained to generate standardized feature vectors even though the underlying data (e.g., patient sequence information 152 and provider sequence information 162) may be different for various patients/providers. For instance, certain patients may have a more extensive patient history than others that recently enrolled in a treatment program, so the number of events within the patient sequence information 152 may vary between patients. In such instances, if patient data does not include a requisite number of events (e.g., 5 events) used to generate a feature vector, then the patient sequence model 154 may nonetheless generate a feature vector even though the patient data may not include the requisite number of events.

For example, the patient sequence model 154 may retrofit the feature vector generation process by introducing blank events (i.e., events with no data) into the patient sequence information 152 so that a feature vector is generated in the same manner as processing patient data with the requisite number of events. In other instances, if the patient sequence information 152 includes extensive data (e.g., greater than 50 events), then the patient sequence model 154 may identify and process only the most relevant events for use in generating a feature vector. For example, only the five most recently occurring events can be processed to generate a feature vector. As another example, only the events that correspond to a type of treatment or specific medication may be used for feature generation. In this way, the patient sequence model 154 and the provider sequence model 164 can develop and apply a standardized procedure for generating feature vectors even though data variability may exist amongst different patients or providers.

In some implementations, the deep learning engine 110 is configured such that the patient sequence model 154 and the provider sequence model 164 are recurrent neural networks, and the entity attribute model 174 and the combining model 182 are deep neural networks. The recurrent neural networks are configured to enable deep sequence embedding to generate features for feature vectors. For example, the patient sequence feature vector 156 includes features that can be used to identify an opportunity patient, and the provider sequence feature vector 166 includes features that can be used to identify an opportunity event. In some instances, the recurrent neural networks are configured as long short-term memory recurrent neural networks (LSTM-RNNs) that enable deep sequence embedding to generate features for medical history. In such instances, the LSTM-RNN can include an input layer, one or more hidden layers, an output layer, a max pooling layer and one or more additional neuron layers.

The deep neural networks are configured to enable sophisticated mathematical modeling for analysis of complex data. For example, the combining model 182 can process features included in the patient sequence feature vector 156, the provider sequence feature vector 166, and the entity-specific feature vectors 174A to compute an opportunity score. In this example, the opportunity score reflects a predicted likelihood that a patient will be classified as an opportunity patient given features identified in the feature vectors. In some instances, the deep neural networks can be configured to enable sophisticated mathematical modeling for analyses of complex data. The deep neural networks can have an input layer representing output from LSTM-RNNs and static features. The deep neural networks can also include one or more hidden layers, and an output layer that is configured to output a predicted score (e.g., a score reflecting a predicted likelihood that a patient is an opportunity patient).

As discussed above, each learning model with the deep learning engine 110 specifies a set of one or more predicted analytics techniques that utilize data patterns and/or trends within electronic data to predict the occurrence of a certain condition (e.g., change to prescribing activity, risk of an adverse event, patient's dissatisfaction with medical treatment). In some instances, each learning model is trained to apply an alternative predictive analytic technique to compute corresponding metrics. In this regard, the system 100 applies a particular learning model from among multiple learning models when computing a metric with respect to a different type of data.

For example, the patient sequence model 154 is trained using a dataset identifying a patient's preference for treatment received, a healthcare practitioner providing treatment, a medication that is being taken, among others. The patient sequence model 154 is therefore trained to identify events identifying a likelihood that a patient prefers a change to a healthcare service (which is then used to identify opportunity patients, as described throughout). As another example, the provider sequence model 164 is trained using a dataset identifying a providers' activity patterns, such as prescribing activity, diagnoses provided, patients examined, among others. The provider sequence model 164 is therefore trained to identify events identifying a likelihood that provider activity is likely to result in an opportunity event (e.g., prescription of a new medication to a patient, diagnosis of a new medical condition, indication of a change to ongoing medical treatment).

The learning models discussed above may be nested or focused. For example, a first model may be used across a first range of values appearing in a database. However, a context (e.g., input values) may be used to develop and invoke a more accurate learning model for those conditions where it is determined that a second learning model aligns with predicted values. That is, an alternative model with weak correlation across a broader range may in fact be associated with a stronger correlation across a subset of triggering conditions. The triggering conditions may be dynamically identified as representing a basis for stronger correlation, and thus, use of a different learning model. The system 100 then may be configured to invoke those triggering conditions to process newly received values using the different learning model. Such a configuration may realize computational efficiencies as the newly introduced learning model is only invoked on a selective basis. Such an invocation also may limit the size storage required as results associated with the different learning model need not be stored for all contexts and inputs.

In some implementations, the deep learning engine 110 is trained using a customized loss function, regularization and dropouts to tune for higher accuracy and avoid overfitting. Graphical Processing Units (GPU) can be used in training to improve speed associated with training.

In some implementations, the deep learning engine 110 includes additional machine learning models to identify drivers and triggers from associated with opportunity patients. As an example, a trigger for an opportunity patient can be an indication that a patient is likely to change a medication associated with a treatment (e.g., in response to being diagnosed with a new medical condition). An example of a driver can be frequent negative feedback provided by a patient, which indicates that he/she is likely to change a provider of healthcare services. The deep learning engine 110 can be trained based on simulated scenarios of these drivers and triggers, to improve its capability to recognize them in production data.

Figure 2:
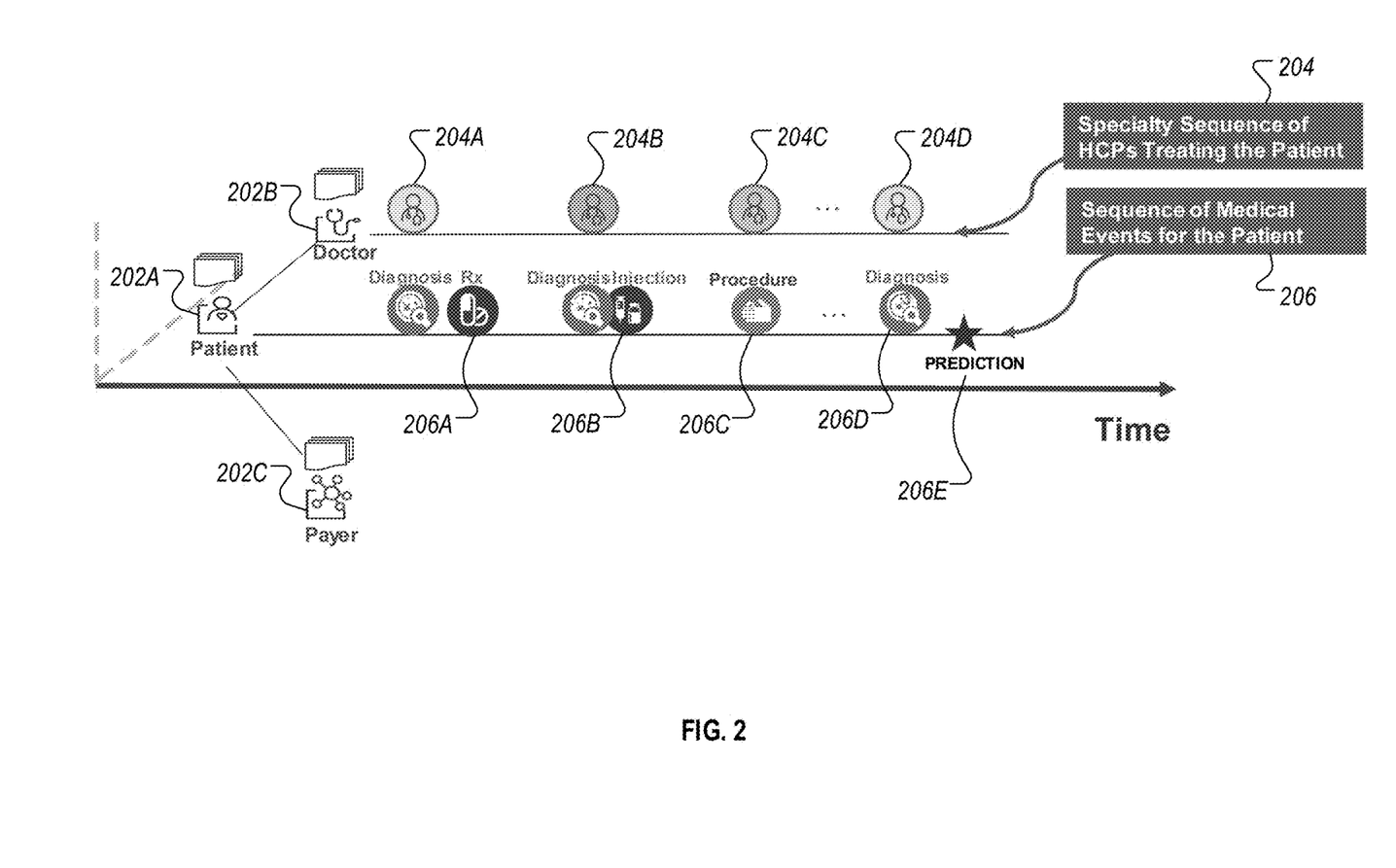
FIG. 2 illustrates examples of sequences that identify events associated with a treatment plan.

FIG. 2 illustrates examples of sequences that identify events associated with a treatment plan. A first sequence associated with a patient 202A (e.g., patient sequence information 152) identifies events detected from a patient's medical history data stored in a database. A second sequence associated with a provider 202B (e.g., provider sequence information 162) identifies events detected from a provider's electronic health records. The patient sequence is also associated with a payer 202C that is associated with a healthcare insurance plan of the patient 202A. In some instances, a third sequence associated with the payer 202C is used to track payer events, such as a patient's submission of a reimbursement claim for treatment received from the provider 202B.

The patient sequence specifies a timeline of events used to track a patient's experience through the treatment plan. For instance, an event 206A represents an initial visit during which the patient 202A is diagnosed to have a disease condition and prescribed a medication by the provider 202B for treatment of the disease condition. Event 206B represents a follow-up visit during which the patient 202A received a refined diagnosis based on laboratory tests performed to evaluate progression of the patient's health condition. Event 206C represents a procedure received on the patient 202A after the follow-up visit during event 206B. Additionally, event 206D represents a new diagnosis received after the medical procedure performed in event 206C.

The provider sequence specifies a timeline of events used to track activity by the provider 202B in relation to treatment received by the patient 202A. Specifically, each event specified in the patient timeline (e.g., events 206A-D) is mapped to a corresponding provider event to enable cross-correlation analysis of provider data and patient data. As shown, event 204A is mapped to event 206A, event 204B is mapped to event 206B, event 204C is mapped to event 206C, and event 204D is mapped to event 206D. Each of the events 204A-D is associated with data collected by the provider 202B during patient visits. For example, event 204D can include a patient chart, a patient questionnaire, and other notes collected by the provider 202B during a patient visit when establishing an initial diagnosis.

As discussed throughout, the system 100 can evaluate sequence information to classify patients as likely representing an opportunity patient. In the example shown in FIG. 2, the deep learning engine 110 (shown in FIG. 1B) can process events specified by the provider sequence (e.g., events 204A-D) and events specified by the patient sequence (e.g., events 206A-D) in parallel to determine the likelihood that patient 202A should be classified as an opportunity patient.

Specifically, the deep learning engine 110 applies patient sequence model 154 to data representing events 206A-D to generate a prediction 204 relating to the provider's activity within the treatment plan. Additionally, the deep learning engine 110 applies provider sequence model 164 to data representing events 204A-D to generate a prediction 206 relating to medical events specified within the treatment plan. The deep learning engine 110 then applies the combining model 182 to combine these two perspectives together and generate a prediction 206E that the patient 202A will obtain a new medication of a specified brand.

In the example shown in FIG. 2, the prediction 206E is used to classify the patient 202A as an opportunity patient given that the deep learning engine 110 predicts him/her to obtain a new medication for treatment. As described throughout, the classification can be used to proactively perform certain operations before the patient 202A collects a medication. The prediction 206E can then be used to predict changes to the patient's treatment plan and preemptively provide corresponding information to a user device of the patient 202A.

For example, the system 100 can output dosage instructions for properly taking the medication, potential side effects of the medication, or advertisements for products associated with the medication, to a user device of the patient 202A. As another example, the system 100 can update the anticipated prescribed volume for the medication so that resource allocation processes more accurately reflect subsequent patient usage of the medication. In yet another example, historical data for other patients that have previously used the medication can be used to determine anticipated impacts on the current treatment of the patient 202A. These anticipated impacts can then be used to predict further downstream impacts to be provided to the user (e.g., impacts on overall treatment outcome, possible changes in side effects to be experienced by the patient, required changes to lifestyle due to medication use).

Figure 3:
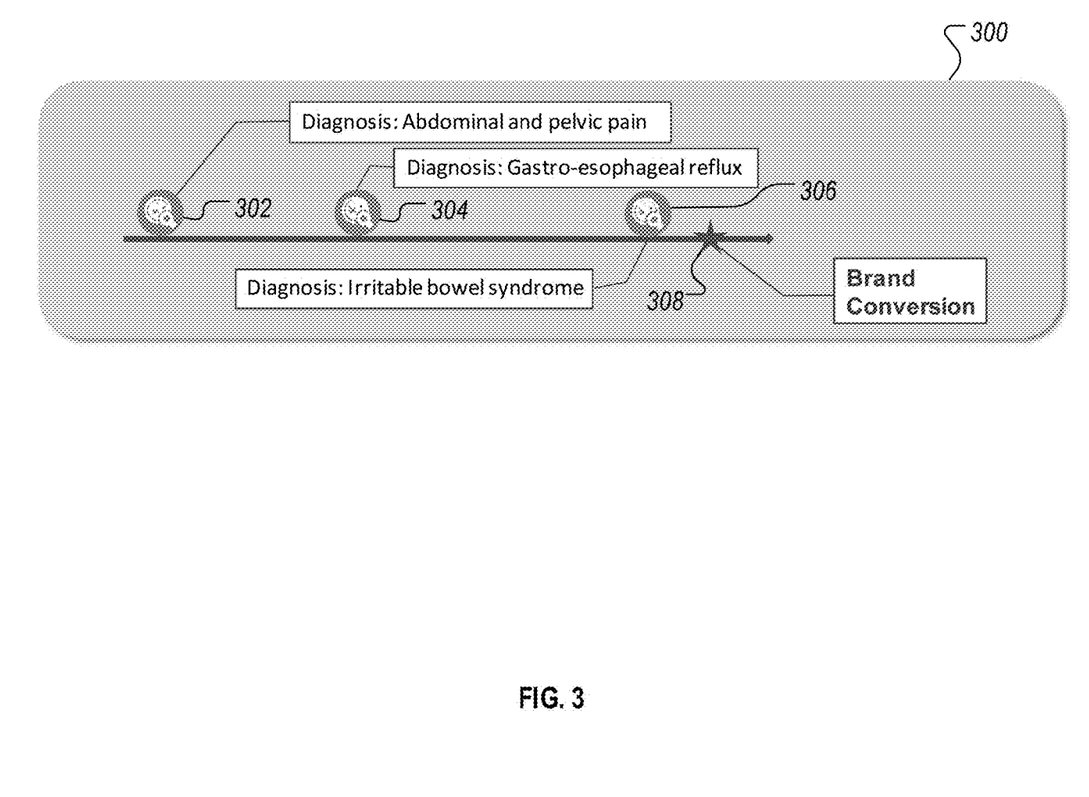
FIG. 3 illustrates an example of a treatment sequence for which an opportunity event is predicted.

FIG. 3 illustrates an example of a treatment sequence 300 for which an opportunity event is predicted. The sequence 300 identifies three events 302, 304, and 306. In this example, each of the three events represent a distinct medical examination during which a patient is provided with a different diagnosis for a chronic condition. At event 302, the patient is initially diagnosed with abdominal and pelvic pain as limited data has been collected to make a more detailed diagnosis. At event 304, the initial diagnosis is updated to gastro-esophageal reflux based on data collected between events 302 and 304 indicating that the patient regularly experienced heartburn. Finally, at event 306, a new diagnosis is issued to reflect that the patient has irritable bowel syndrome. The diagnosis issued at event 306, though more refined, represents a distinct condition relative to the diagnosis issued at event 304. Because of this adjustment, the patient is predicted to have changes to his/her treatment plan that also impacts the medications (or the brands of medications) he/she uses as a part of his/her treatment plan.

The system 100 predicts an opportunity event 308 based on the differences in the diagnoses between events 304 and 306. Specifically, the opportunity event 308 is determined to indicate that the patient will use a different brand of medications given the change in diagnoses. In this way, the opportunity event 308 is used to forecast changes to user behaviors and identify actions that can be performed based on the forecasted changes. For example, the opportunity event 308 is used to classify the patient as an opportunity patient, and then transmit information for medications related to irritable bowel syndrome (before the patient actually obtains medications). In this example, patient classification enables the system 100 to preemptively provide useful information to a patient before he/she makes a decision to adjust medications based on updates to his/her diagnosed condition.

Figure 4:
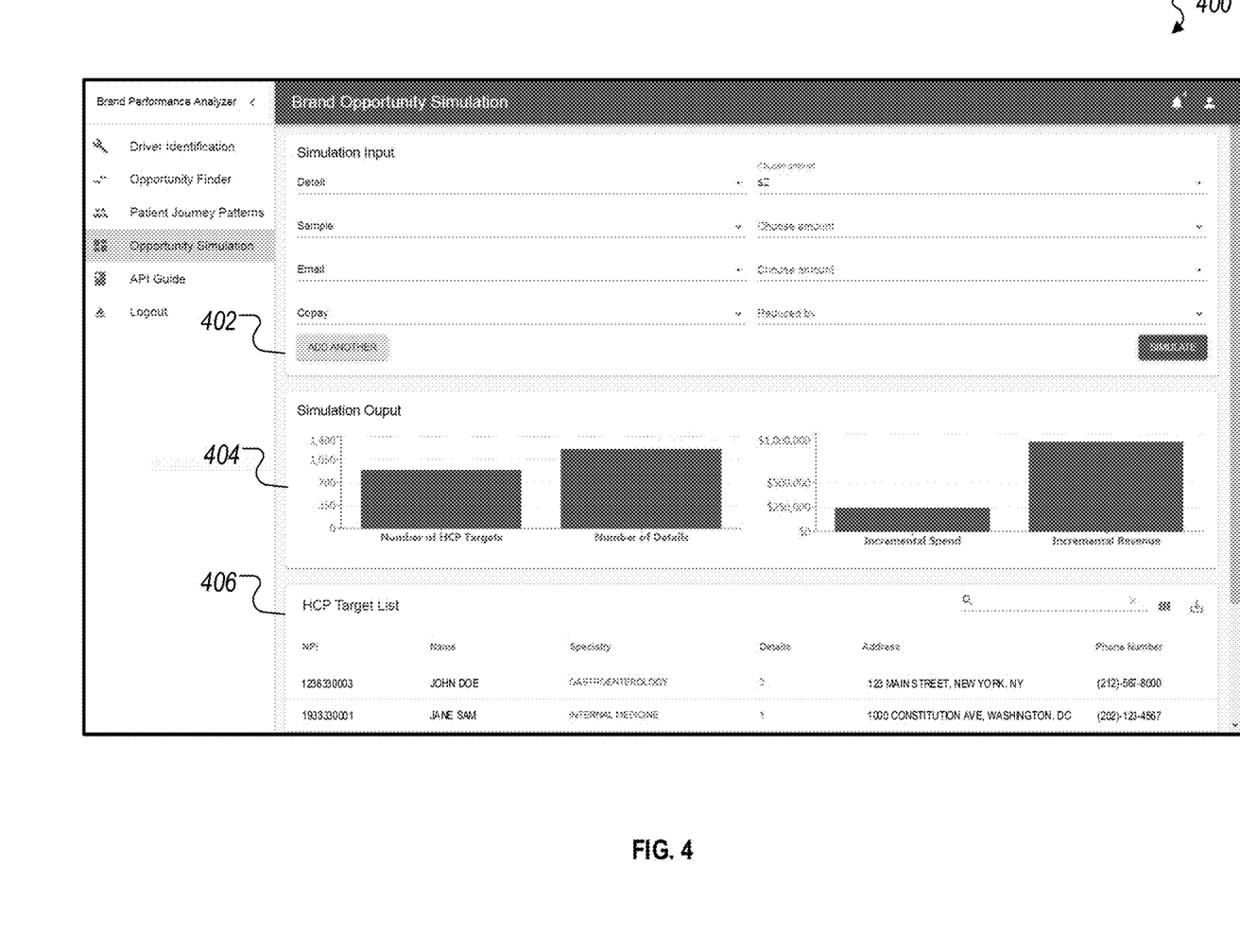
FIG. 4 illustrates an example of an interface for managing data associated to opportunity events predicted by a deep learning engine.

FIG. 4 illustrates an example of an interface 400 for managing data associated to opportunity events predicted by the deep learning engine 110. In this example, the interface 400 is used to enable a user (e.g., an employee of a pharmaceutical manufacturer or pharmaceutical distributor) to evaluate performance of brands of medication that are prescribed to patients. Performance, in this context, can refer to pharmaceutical sales volume, prescription volume, prescription frequency over a specified time period, among other types of metrics.

Interface 400 enables a user to identify opportunities to stimulate a certain brand of medications based on data generated by the system 100 relating to opportunity events. Opportunity events can reflect predicted changes to prevalence of a medication brand, which can then be used to simulate marketing actions to optimize brand performance. For example, opportunity patients that are predicted to change existing medications to start taking the medication brand can be targeted using marketing actions to improve adoption of the medication brand. As previously noted, the opportunity patients can be targeted before they decide to change medications so that the likelihood of user adoption is increased.

As shown in FIG. 4, the interface 400 includes an interface element 402 enabling a user can input information related to a targeting strategy (e.g., based on amount of a medication used, amount of copay). Interface element 404 displays a simulation of predicted outcomes of the targeting strategy, for example, the number of providers that are likely to be successfully targeted based on the targeting strategy, and the number of patients that are similarly likely to be successfully targeted. Interface element 404 also displays evaluation parameters of the targeting strategy, such as a predicted incremental cost in implementing the targeting strategy, and a predicted incremental revenue increase resulting from the targeting strategy. In this way, the user can use information displayed in interface element 404 to determine whether a targeting strategy is predicted to be successful (e.g., incremental revenue predicted to exceed incremental cost) or unsuccessful (e.g., incremental cost predicted to exceed incremental revenue).

Interface 406 identifies a list of opportunity providers that can potentially be targeted using the targeting strategy specified in interface element 402. The opportunity providers can be identified by the deep learning engine 110 using techniques described throughout. For example, the opportunity providers can be those that are identified to have recently diagnosed and/or treatment patients with disease conditions that are typically treated using a target medication. In other examples, the opportunity patients can be those that have been newly affiliated with a provider network and not yet established preferences for prescribing activity (e.g., providers that have not yet developed a preferred medication brand for treating a certain disease condition).

Figure 5:
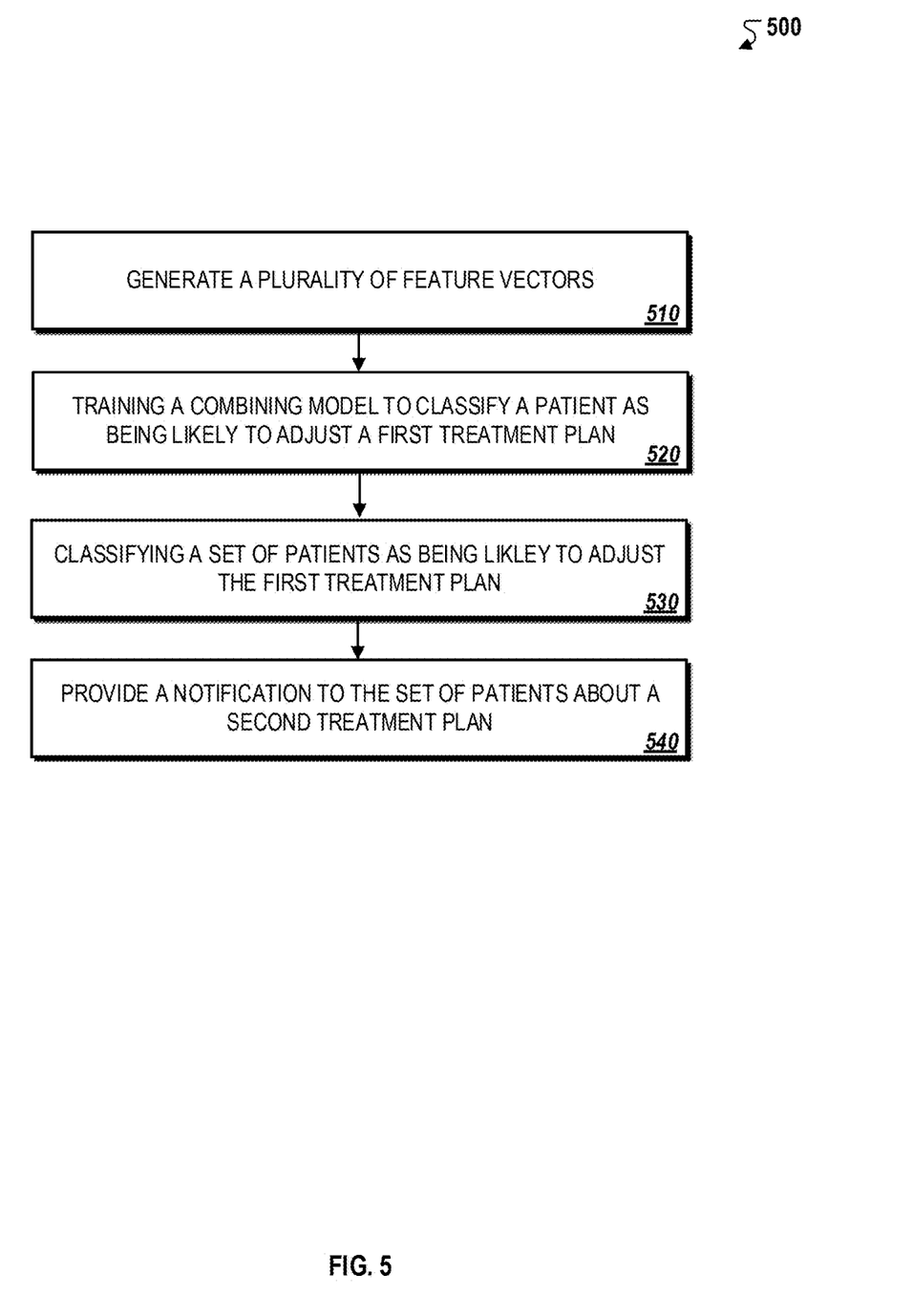
FIG. 5 illustrates an example of a process for identifying opportunity patients based on applying a deep learning engine to recognize patterns within integrated patient data.

FIG. 5 illustrates an example of a process 500 for identifying opportunity patients based on applying a deep learning engine to recognize patterns within integrated patient data. Briefly, the process 500 can include the operations of generating a plurality of feature vectors (510), training a combining model to classify a patient as being likely to adjust a first treatment plan (520), classifying a set of patients as being likely to adjust the first treatment plan (530), and providing a notification indicating the set of patients for output (540).

In general, the process 500 is described below in reference to system 100, although other systems can be configured to execute the process 500. In one example, the process 500 can be performed by a system that includes multiple machine learning models (e.g., patient sequence model 154, provider sequence model 164, entity attribute model 174, combining model 182) that each are implemented in a separate computing device. In this example, the system can include a set of computing devices that are configured to implement software that executes the steps of the process 500 discussed below.

Additionally, although the steps of the process 500 are discussed below as being performed sequentially, in some implementations, one or more steps of the process 500 can be performed in parallel to improve, for example, the speed associated with identifying opportunity patients 120. For example, in some instances, certain steps of the process 500 can be executed in parallel (e.g., using distinct computing devices that each implement a different machine learning model, or a single computing device configured to run the different machine learning models in parallel) to reduce the time necessary to generate feature vectors (e.g., patient sequence feature vector 156, provider sequence feature vector 166, and entity attribute model 174). In such instances, the identification of opportunity patients can be performed based on the respective outputs of previous steps that are executed in parallel. In other instances, the steps are executed sequentially as discussed below.

In more detail, the process 500 can include the operations of generating a plurality of feature vectors (510). As discussed throughout, the plurality of feature vectors can include a patient sequence feature vector, a provider sequence feature vector, and a set of entity-specific feature vectors. Each of these vectors can be processing corresponding data, as detailed below.

The plurality of feature vectors can be generated based on obtaining integrated patient data. For example, the system 100 can obtain integrated patient data 102 for a plurality of patients. The integrated patient data 102 can include data obtained from multiple different data sources, such as longitudinal patient data 102A, provider key performance indicators 102B, patient reference data 102C, client promotion data 102D, and longitudinal access and adjudication data 102E. The integrated patient data 102 can also be processed to identify specific types of aggregated data. For example, as shown in FIG. 1B, the integrated patient data 102 can include patient sequence information 152 identifying treatment events associated with a treatment plan (e.g., events 206A-D in FIG. 2). Also shown in FIG. 1B, is provider sequence information identifying providers that have participated in a treatment event associated with the treatment plan (e.g., events 204A-D in FIG. 2). Additionally, the integrated patient data 102 includes a set of entity-specific attributes associated with the treatment plan, such as provider-level attributes 172A, patient-level attributes 172B, payer-level attributes 172C, and plan-level attributes 172D (shown in FIG. 1B).

The plurality of feature vectors can include a patient sequence feature vector. For example, the system 100 can generate a patient sequence feature vector 156 corresponding to the patient sequence information 152 based on applying the patient sequence model 154 to the patient sequence information 152. As described in reference to FIG. 1B, the patient sequence model 154 is trained to output the patient sequence feature vector 156 by identifying data patterns and/or trends that indicate that a patient is likely to make a change to a healthcare service (e.g., a change to medication used in a treatment plan). For example, the patient sequence feature vector 156 can identify a likelihood that medical history patterns identified in the patient sequence information 152 is predictive of a patient seeking a new treatment medication. As examples, the patient sequence information 152 can specify patterns related to long term drug therapy, a patient seeking psychotherapy services, or receiving diagnoses associated with high likelihood of a change to treatment. In these examples, the patient sequence model 156 recognizes the presence of patterns indicating, for instance, that a patient is dissatisfied with the medication being used to provide treatment of a disease condition and thereby likely to adjust the medication.

The plurality of feature vectors can additionally include a provider sequence feature vector. For example, the system 100 can generate a provider sequence feature vector 166 corresponding to the provider sequence information 162 based on applying the provider sequence model 164 to the provider sequence information 162. As described in reference to FIG. 1B, the provider sequence model 164 is trained to output the provider sequence feature vector 166 by identifying data patterns and/or trends that indicate that a provider is likely to make a change to how he/she treats patients (e.g., a change to prescribing activity to include a new medication). For example, the patient sequence feature vector 166 can identify a likelihood that provider data identified in the provider sequence information 162 is predictive of a patient seeking a new provider. As examples, the provider sequence information 162 can specify treatment events related to diagnosis of a disease condition, injections administered, medical procedures performed, diagnoses rendered, prescribed medications, or prescription adjustments. In these examples, the provider sequence model 164 recognizes the presence of patterns indicating, for instance, that a patient is dissatisfied with the medical service provided by an existing provider and thereby likely to adjust a provider that provides medical service.

The plurality of feature vectors can also include a set of entity-specific feature vectors. For example, the system 100 can generate entity-specific feature vectors 174A based on applying the entity attribute model 174 to the entity-specific attributes. As described in reference to FIG. 1B, the entity attribute model 174 is trained to output the entity-specific feature vectors 174A by identifying attributes that are likely to be associated with an opportunity patient. For example, if the patient-level attributes 172B identifies many changes made to a patient's healthcare plan, then the entity attribute model 174 determines a higher likelihood that the patient will be classified as an opportunity patient. As another example, if the provider-level attributes 172A identifies many types of prescribing patterns for a provider, then the entity attribute model 174 similarly determines a higher likelihood that the provider will be associated with an opportunity event.

The process 500 can include the operation of training a combining model to classify a patient as being likely to adjust a first treatment plan (520). For example, the system 100 can train the combining model 182 to identify opportunity patients 120 from among multiple patients associated with the integrated patient data 102. The opportunity patients 120 can be identified by applying the combining model 182 to the patient sequence feature vector 156, the provider sequence feature vector 166, and entity-specific feature vectors 174A. As described in reference to FIG. 1B, the combining model is trained to classify patients as representing an opportunity patient (i.e., a patient likely to adjust a treatment plan).

The process 500 can include the operation of classifying a set of patients as being likely to adjust the first treatment plan (530). For example, the combining model 182 can be used to classify a set of patients (e.g., opportunity patients), from the patients associated with the integrated patient data 102, as being likely to adjust the first treatment plan.

The classification can be based on combining probabilistic sub-scores into a combined score representing an overall likelihood that a patient is an opportunity patient. As an example, the sub-scores can include a first sub-score representing a likelihood that patient sequence information includes an opportunity event, a second sub-score representing a likelihood that provider sequence information includes an opportunity event, and a third sub-score representing a degree of similarity between attributes of the patient and attributes of other patients that were previously classified by an entity to receive predictive metrics as being opportunity patients. For example, if the entity to receive the data predictions generated by the deep learning engine 110 is a prescription manufacturer, then the third sub-score can represent a similarity to patients that have adjusted their medication. Alternatively, if the entity to receive the data predictions generated by the deep learning engine 110 is a health management provider, then the third sub-score can represent a similarity to patients that have changed their treatment provider. In the example discussed above, the three sub-scores can be combined to generate an overall likelihood that the patient is classified as an opportunity patient (e.g., if the score exceeds a threshold value of 0.65).

The process 500 can include the operation of transmitting a notification to the set of patients about a second treatment plan (540). For example, the system 100 can provide a notification to the opportunity patients to adjust a present treatment plan such that the adjusted treatment plan represents a second treatment plan. As one example, if an opportunity patient is predicted to make a change to a medication included in a present treatment plan, the system can provide a notification to a client device of the opportunity patient that identifies a different medication that is predicted to be more likely to be used by the patient. As another example, if an opportunity patient is predicted to make a change to a healthcare provider, then the system can provide a notification that identifies another healthcare provider that is, for instance, located in a geographic location of the patient, or is included in a provider network of the treatment plan. In these examples, aspects of the second treatment plan (e.g., new medication, new healthcare provider) can be identified based on predictions generated by the combining model 182 relating to patient behaviors. For example, if healthcare data generate for a given opportunity patient indicates a high likelihood that the patient may have a preference for a new medication that is not being currently prescribed, then the system may recommend a second treatment plan that substitutes the new medication for the current medication.

In some implementations, the system may transmit data indicating the set of patients for output to other end-users. For example, the outputted dated include a list of opportunity patients. As discussed in reference to FIG. 4, in some instances, the list of opportunity patients (or, in some instances, list of opportunity providers) can be used to improve a targeting strategy to improve brand recognition, for instance, for a medication, a treatment plan, among other categories of information. The end-users can be providers that provide treatment to patients, insurance companies or other payers associated with a treatment plan, or employees of other entities associated with the treatment plan (e.g., pharmaceutical manufacturers, pharmaceutical distributers, pharmacies).

Figure 6:
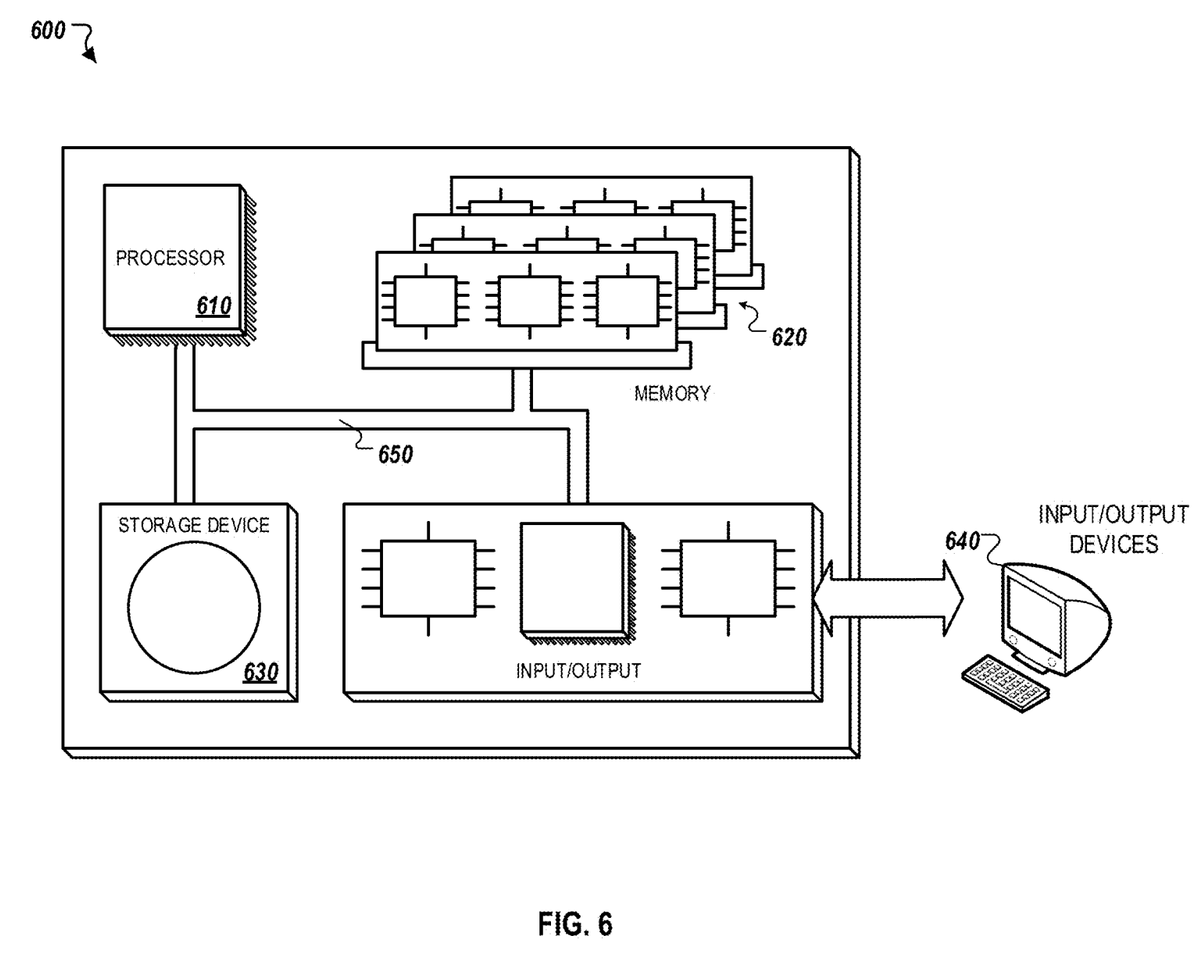
FIG. 6 illustrates an example of computing devices on which the processes described herein, or portions thereof, may be implemented.

FIG. 6 is a schematic diagram of a computer system 600. The system 600 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 600) and their structural equivalents, or in combinations of one or more of them. The system 600 is intended to include various forms of digital computers, such as laptops, desktops, workstations, personal digital assistants, servers, blade servers, mainframes, and other appropriate computers, including vehicles installed on base units or pod units of modular vehicles. The system 600 can also include mobile devices, such as personal digital assistants, cellular telephones, smartphones, and other similar computing devices. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 600 includes a processor 610, a memory 620, a storage device 630, and an input/output device 640. Each of the components 610, 620, 630, and 640 are interconnected using a system bus 640. The processor 610 is capable of processing instructions for execution within the system 600. The processor may be designed using any of several architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical data for a user interface on the input/output device 640.

The memory 620 stores data within the system 600. In one implementation, the memory 620 is a computer-readable medium. In one implementation, the memory 620 is a volatile memory unit. In another implementation, the memory 620 is a non-volatile memory unit.

The storage device 630 can provide mass storage for the system 600. In one implementation, the storage device 630 is a computer-readable medium. In various implementations, the storage device 630 may be a floppy disk device, a hard disk device, an optical disk device, or a tape device.

The input/output device 640 provides input/output operations for the system 600. In one implementation, the input/output device 640 includes a keyboard and/or pointing device. In another implementation, the input/output device 640 includes a display unit for displaying graphical user interfaces.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

Several embodiments have been described. Nevertheless, it will be understood that various modifications may be made without departing from the spirit and scope of the invention. In addition, the logic flows depicted in the figures do not require the order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method, the method comprising:
    obtaining patient sequence information identifying treatment events associated with a first treatment plan and provider sequence information identifying providers that have participated in a treatment event associated with the first treatment plan;
    generating a plurality of feature vectors, including:
        generating a patient sequence feature vector corresponding to the patient sequence information based on applying a first model to the patient sequence information, wherein the first model is trained to output patient sequence feature vectors for respective patients with different patient sequences;
        generating a provider sequence feature vector corresponding to the provider sequence information based on applying a second model to the provider sequence information, wherein the second model is trained to output provider sequence feature vectors for respective providers with different provider sequences;
    training a combining model to classify a patient as being likely to adjust the first treatment plan;
    providing at least some of the plurality of feature vectors as an input to the combining model;
    classifying, based on the combining model, a set of patients as being likely to adjust the first treatment plan; and
    transmitting a notification to the set of patients about a second treatment plan.

2. The method of claim 1, wherein:
    the first treatment plan represents treatment of a disease condition using a pharmaceutical product;
    the patient sequence information identifies, for each patient, a first treatment event indicating diagnosis of the disease condition, a second treatment event indicating a prescription of the pharmaceutical product, and a third treatment event indicating a treatment follow-up; and
    the set of patients represents patients that are classified by the combining model as being likely to withdraw from the first treatment plan based on data associated with the first treatment event, the second treatment event, or the third treatment event.

3. The method of claim 1, wherein generating the plurality of feature vectors comprises generating a set of entity-specific feature vectors corresponding to a set of entity-specific attributes based on applying a third model to the set of entity-specific attributes, wherein the third model is trained to output sets of entity-specific feature vectors for respective sets of entity-specific attributes.

4. The method of claim 3, wherein:
    the first model and the second model each comprise recurrent neural networks; and
    the third model and the combining model each comprise deep neural networks.

5. The method of claim 3, wherein:
    the set of entity-specific attributes comprises provider-level attributes, patient-level attributes, and plan-level attributes; and
    the set of entity-specific feature vectors comprises a provider-level feature vector, a patient-level feature vector, and a plan-level feature vector.

6. The method of claim 1, comprising:
    training the combining model to classify a provider as being likely to adjust the first treatment plan.

7. The method of claim 1, wherein the set of patients comprises one or more patients classified by the combining model as being likely to adjust a pharmaceutical product associated with the first treatment plan.

8. The method of claim 1, wherein the set of patients comprises one or more patients classified by the combining model as being likely to adjust a provider associated with the first treatment plan.

9. A system comprising:
    one or more computing devices; and
    a non-transitory computer-readable storage device storing instructions that are executable by the one or more computing devices to perform operations comprising:
        obtaining patient sequence information identifying treatment events associated with a first treatment plan and provider sequence information identifying providers that have participated in a treatment event associated with the first treatment plan;
        generating a plurality of feature vectors, including:
            generating a patient sequence feature vector corresponding to the patient sequence information based on applying a first model to the patient sequence information, wherein the first model is trained to output patient sequence feature vectors for respective patients with different patient sequences;
            generating a provider sequence feature vector corresponding to the provider sequence information based on applying a second model to the provider sequence information, wherein the second model is trained to output provider sequence feature vectors for respective providers with different provider sequences;
        training a combining model to classify a patient as being likely to adjust the first treatment plan;

training a combining model to classify a patient as being likely to adjust the first treatment plan;

providing at least some of the plurality of feature vectors as an input to the combining model;

classifying, based on the combining model, a set of patients as being likely to adjust the first treatment plan; and transmitting a notification to the set of patients about a second treatment plan.

10. The system of claim 9, wherein:

the first treatment plan represents treatment of a disease condition using a pharmaceutical product;

the patient sequence information identifies, for each patient, a first treatment event indicating diagnosis of the disease condition, a second treatment event indicating a prescription of the pharmaceutical product, and a third treatment event indicating a treatment follow-up; and the set of patients represents patients that are classified by the combining model as being likely to withdraw from the first treatment plan based on data associated with the first treatment event, the second treatment event, or the third treatment event.

11. The system of claim 9, wherein generating the plurality of feature vectors comprises generating a set of entity-specific feature vectors corresponding to a set of entity-specific attributes based on applying a third model to the set of entity-specific attributes, wherein the third model is trained to output sets of entity-specific feature vectors for respective sets of entity-specific attributes.

12. At least one non-transitory computer-readable storage device storing instructions that are executable by one or more computing devices to perform operations comprising:

obtaining patient sequence information identifying treatment events associated with a first treatment plan and provider sequence information identifying providers that have participated in a treatment event associated with the first treatment plan;

generating a plurality of feature vectors, including:

generating a patient sequence feature vector corresponding to the patient sequence information based on applying a first model to the patient sequence information, wherein the first model is trained to output patient sequence feature vectors for respective patients with different patient sequences;

generating a provider sequence feature vector corresponding to the provider sequence information based on applying a second model to the provider sequence information, wherein the second model is trained to output provider sequence feature vectors for respective providers with different provider sequences;

training a combining model to classify a patient as being likely to adjust the first treatment plan;

providing at least some of the plurality of feature vectors as an input to the combining model;

classifying, based on the combining model, a set of patients as being likely to adjust the first treatment plan; and transmitting a notification to the set of patients about a second treatment plan.

13. The one non-transitory computer-readable storage device of claim 12, wherein:

the first treatment plan represents treatment of a disease condition using a pharmaceutical product;

the patient sequence information identifies, for each patient, a first treatment event indicating diagnosis of the disease condition, a second treatment event indicating a prescription of the pharmaceutical product, and a third treatment event indicating a treatment follow-up; and the set of patients represents patients that are classified by the combining model as being likely to withdraw from the first treatment plan based on data associated with the first treatment event, the second treatment event, or the third treatment event.

14. The one non-transitory computer-readable storage device of claim 12, wherein generating the plurality of feature vectors comprises generating a set of entity-specific feature vectors corresponding to a set of entity-specific attributes based on applying a third model to the set of entity-specific attributes, wherein the third model is trained to output sets of entity-specific feature vectors for respective sets of entity-specific attributes.

* * * * *

UNITED STATES PATENT AND TRADEMARK OFFICE
CERTIFICATE OF CORRECTION

PATENT NO. : 11,328,825 B1  
APPLICATION NO. : 16/847562  
DATED : May 10, 2022  
INVENTOR(S) : Yu et al.

Page 1 of 1

It is certified that error appears in the above-identified patent and that said Letters Patent is hereby corrected as shown below:

In the Claims

Column 18, Claim 9:
Lines 66-67, after "sequences;" delete "training a combining model to classify a patient as being likely to adjust the first treatment plan;".

Signed and Sealed this
Twenty-eighth Day of June, 2022

Katherine Kelly Vidal
*Director of the United States Patent and Trademark Office*